US012768839B2

(12) United States Patent
Probst et al.

(10) Patent No.: US 12,768,839 B2
(45) Date of Patent: Oct. 20, 2026

(54) ANALYTE DETECTION USING ELECTROCHEMICAL IMPEDANCE SPECTROSCOPY-BASED IMAGINARY IMPEDANCE MEASUREMENT

(71) Applicant: ARIZONA BOARD OF REGENTS ON BEHALF OF ARIZONA STATE UNIVERSITY, Scottsdale, AZ (US)

(72) Inventors: David Probst, Tempe, AZ (US); Chi Lin, Van Nuys, CA (US); Marcus Smith, Birmingham, AL (US); Jeffrey LaBelle, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 865 days.

Patent file contains an affidavit/declaration under 37 CFR 1.130(b).

(21) Appl. No.: 18/084,320

(22) Filed: Dec. 19, 2022

(65) Prior Publication Data

US 2023/0184755 A1 Jun. 15, 2023

Related U.S. Application Data

(62) Division of application No. 16/495,682, filed as application No. PCT/US2018/023375 on Mar. 20, 2018, now Pat. No. 11,549,904.

(Continued)

(51) Int. Cl.

*G01N 33/543* (2006.01)
*G01N 27/02* (2006.01)

(Continued)

(52) U.S. Cl.

CPC ......... *G01N 33/5438* (2013.01); *G01N 27/02* (2013.01); *G01N 27/026* (2013.01);

(Continued)

(58) Field of Classification Search

CPC .. G01N 33/5438; G01N 27/02; G01N 27/026; G01N 27/3275; G01N 33/543;

(Continued)

(56) References Cited

U.S. PATENT DOCUMENTS 7,067,293 B2 6/2006 LaBelle et al.
8,815,178 B2 8/2014 Bishop et al.

(Continued)

FOREIGN PATENT DOCUMENTS

WO 2004023099 A2 3/2004
WO 2010111484 A1 9/2010

(Continued)

OTHER PUBLICATIONS

Adamson, T. L. et al. Detection of 1,5-Anhydroglucitol by Electrochemical Impedance Spectroscopy. J. Diabetes Sci. Technol. 2014, 8 (2), 350-355.

(Continued)

*Primary Examiner* — Christopher L Chin
*Assistant Examiner* — Ellis Follett Lusi
(74) *Attorney, Agent, or Firm* — Quarles & Brady LLP

(57) ABSTRACT

Methods for detecting one or more analytes in a sample utilizing Electrochemical Impedance Spectroscopy (EIS) measurement. In one method, analyte detection includes comparing an imaginary impedance measurement to a calibration curve of concentrations for each target analyte. The calibration curve of concentrations for each target analyte is established at an optimal frequency. In another method, a (Continued)

signal decoupling algorithm is utilized for detection of more than one analyte on an electrode.

16 Claims, 9 Drawing Sheets

Related U.S. Application Data

(60) Provisional application No. 62/473,894, filed on Mar. 20, 2017.

(51) Int. Cl.
*G01N 27/327* (2006.01)
*G01N 33/92* (2006.01)

(52) U.S. Cl.
CPC ....... *G01N 27/3275* (2013.01); *G01N 33/543* (2013.01); *G01N 33/54353* (2013.01); *G01N 33/92* (2013.01)

(58) Field of Classification Search
CPC ............. G01N 33/54353; G01N 33/92; G01N 27/3276; G01N 27/00; G01N 27/22; G01N 27/327; A61B 5/1468; A61B 5/150022; A61B 5/150358
USPC ............ 204/403.01, 412, 403.06; 422/82.01; 435/287.2; 436/524, 501, 806
See application file for complete search history.

(56) References Cited

U.S. PATENT DOCUMENTS

| | | | | |
|---|---|---|---|---|
| 9,532,747 | B2 | 1/2017 | LaBelle et al. | |
| 10,386,321 | B2 | 8/2019 | LaBelle et al. | |
| 10,724,066 | B2 | 7/2020 | LaBelle et al. | |
| 2006/0263836 | A1 | 11/2006 | Connelly et al. | |
| 2010/0010325 | A1 | 1/2010 | Ridder et al. | |
| 2012/0037515 | A1 | 2/2012 | Solanki | |
| 2012/0244547 | A1* | 9/2012 | Mazzari | G01N 27/126 435/7.1 |
| 2012/0285829 | A1 | 11/2012 | Mount et al. | |
| 2013/0183243 | A1 | 7/2013 | Labelle et al. | |
| 2014/0311904 | A1 | 10/2014 | Rozlosnik et al. | |
| 2015/0057513 | A1 | 2/2015 | LaBelle et al. | |
| 2015/0276637 | A1 | 10/2015 | Prasad et al. | |
| 2019/0046092 | A1 | 2/2019 | LaBelle et al. | |
| 2019/0150815 | A1 | 5/2019 | LaBelle et al. | |
| 2019/0234816 | A1 | 8/2019 | LaBelle et al. | |
| 2019/0369042 | A1 | 12/2019 | LaBelle et al. | |
| 2020/0011778 | A1 | 1/2020 | Honikel et al. | |
| 2020/0354764 | A1 | 11/2020 | LaBelle et al. | |
| 2021/0233196 | A1 | 7/2021 | Qin et al. | |

FOREIGN PATENT DOCUMENTS

| | | | |
|---|---|---|---|
| WO | 2012009322 | A1 | 1/2012 |
| WO | 2013172929 | A1 | 11/2013 |
| WO | 2014022586 | A1 | 2/2014 |
| WO | 2016025153 | A1 | 2/2016 |
| WO | 2017132565 | A1 | 8/2017 |
| WO | 2018067626 | A1 | 4/2018 |
| WO | 2018148236 | A1 | 8/2018 |
| WO | 2018208610 | A1 | 11/2018 |
| WO | 2019178588 | A1 | 9/2019 |

OTHER PUBLICATIONS

Adamson, T. L. et al. The Promise of Electrochemical Impedance Spectroscopy as Novel Technology for the Management of Patients with Diabetes Mellitus. Analyst 2012, 137 (18), 4179-4187.

Baudouin, C. et al. Correlation between Tear IgE Levels and HLA-DR Expression by Conjunctival Cells in Allergic and Nonallergic Chronic Conjunctivitis. Graefes Arch. Clin. Exp. Ophthalmol. 2000, 238 (11), 900-904.

Beckman, K. A. et al. Making the Diagnosis of Sjögren's Syndrome in Patients with Dry Eye. Clin. Ophthalmol. Auckl. NZ 2016, 10, 43.

Boonyasit Y et al. A multiplexed three-dimensional paper-based electrochemical impedance device for simultaneous label-free affinity sensing of total and glycated haemoglobin: the potential of using a specific single frequency value for analysis. Analytica Chimca Acta. 2016. 936: 1-11. DOI: 10.1016/j.aca.2016.05.047.

Bravo-Anaya LM et al. The scaling of electrochemical parameter of DNA aqueous solutions with concentration and temperature through an electrochemical impedance spectroscopy study. Electrochimica Acta. 2015. 167:311-320. DOI: 10.1016/j.electacta.2015.03.106.

Campos, Hannia, et al. "LDL particle size distribution. Results from the Framingham Offspring Study." Arteriosclerosis and Thrombosis: A Journal of Vascular Biology 12.12 (1992): 1410-1419.

Cardinell, B. A. et al. Enzymatic Detection of Traumatic Brain Injury Related Biomarkers. Biosens. Biodetection Methods Protoc. vol. 2 Electrochem. Bioelectron. Piezoelectric Cell. Mol. Biosens. 2017, 89-112. First available online Mar. 16, 2017.

Chin, C. D. et al. Commercialization of Microfluidic Point-of-Care Diagnostic Devices. Lab. Chip 2012, 12 (12), 2118-2134.

D'Souza, S. et al. Practical Issues Concerning Tear Protein Assays in Dry Eye. Eye Vis. 2014, 1 (1), 6.

De Boer, R. A., et al. "Predictive value of plasma galectin-3 levels in heart failure with reduced and preserved ejection fraction." Annals of medicine 43.1 (2011): 60-68.

Demirok Uk et al. The development of a label-free electrochemical impedance based point-of-care technology for multimarker detection. Journal of Biosensors & Bioelectronics. 2013, S12. DOI: 10.4172/2155-6210.S12-004.

Dumortier, G. et al. Lachrymal Determinations: Methods and Updates on Biopharmaceutical and Clinical Applications. Ophthalmic Res. 2004, 36 (4), 183-194.

Esfandyarpour R et al. Nanoelectronic three-dimensional (3D) nanotip sensing array for real-time, sensitive, abel-free sequence specific detection of nucleic acids. Biomed Microdevices. 2016. 18:7. DOI: 10.1007/s10544-016-0032-8.

Expert Panel on Detection, Evaluation. "Executive summary of the third report of the National Cholesterol Education Program (NCEP) expert panel on detection, evaluation, and treatment of high blood cholesterol in adults (Adult Treatment Panel III)." Jama 285.19 (2001): 2486.

Fernandez, M. L. et al. "The LDL to HDL cholesterol ratio as a valuable tool to evaluate coronary heart disease risk." Journal of the American College of Nutrition 27.1 (2008): 1-5.

Fomo, G. et al. Aptameric Recognition-Modulated Electroactivity of Poly (4-Styrenesolfonic Acid)-Doped Polyaniline Films for Single-Shot Detection of Tetrodotoxin. Sensors 2015, 15 (9), 22547-22560.

Food and Drug Administration. Guidance for Industry on Bioanalytical Method Validation. Fed. Regist. 2001, 66 (100), 28526.

Foulks, G.N. et al., 1994. Rapid Measurement of Selected Tear Proteins in Health and Disease Using the Touch Tear Microassay System, in: Lacrimal Gland, Tear Film, and Dry Eye Syndromes. Springer, pp. 371-375.

Fujishima, H. et al. Allergic Conjunctivitis and Dry Eye. Br. J. Ophthalmol. 1996, 80 (11), 994-997.

Giacometti JA et al. Impedance of aqueous solution of KCl at the ultra-low frequency range: use of cole-cole impedance element to account for the frequency dispersion peak at 20 mHz. Brazilian Journal of Physics. 2016. 46:50-55. DOI: 10.1007/s13538-015-0381-4.

Gouveia-Caridade, C et al. "Electrochemical impedance characterization of Nation-coated carbon film resistor electrodes for electroanalysis." Electroanalysis. 17.7 (2005): 549-555.

Hagan, S. et al. Tear Fluid Biomarkers in Ocular and Systemic Disease: Potential Use for Predictive, Preventive and Personalised Medicine. EPMA J. 2016, 7.

Halade, G. V. et al. Matrix Metalloproteinase (MMP)-9: A Proximal Biomarker for Cardiac Remodeling and a Distal Biomarker for Inflammation. Pharmacol. Ther. 2013, 139 (1), 32-40.

(56) References Cited

OTHER PUBLICATIONS

Hamilton, R. G. Accuracy of US Food and Drug Administration-cleared IgE Antibody Assays in the Presence of Anti-IgE (Omalizumab). J. Allergy Clin. Immunol. 2006, 117 (4), 759-766.
Hernandez, K. et al. Control of Protein Immobilization: Coupling Immobilization and Site-Directed Mutagenesis to Improve Biocatalyst or Biosensor Performance. Enzyme Microb. Technol. 2011, 48 (2), 107-122.
Hirschorn, B., et al. "Determination of effective capacitance and film thickness from constant-phase-element parameters." Electrochimica acta 55.21 (2010): 6218-6227.
Hojberg J et al. An electrochemical impedance spectroscopy investigation of the overpotential in Li—O2 batteries. Applied Materials & Interfaces. 2015. 7:4039-4047. DOI: 10.1021/am5083254.
Hom, M. M. et al. Allergic Conjunctivitis and Dry Eye Syndrome. Ann. Allergy Asthma Immunol. Off. Publ. Am. Coll. Allergy Asthma Immunol. 2012, 108 (3), 163-166.
Hsu, C. H., et al. "Concerning the conversion of the constant phase element parameter Y0 into a capacitance." Corrosion 57.9 (2001): 747-748.
Hui G-H et al. Electrochemical Impedance Spectrum Frequency Optimization of Bitter Taste Cell Based Sensors. Biosensors and Bioelectronics. 2013. 47:164-170.
International Searching Authority. International Search Report and Written Opinion for application PCT/US2018/023375. Mailed on Jun. 6, 2018.
Jeyarajah, E. J., et al. "Lipoprotein particle analysis by nuclear magnetic resonance spectroscopy." Clinics in laboratory medicine 26.4 (2006): 847-870.
Kochowski, S. et al. "Description of the frequency behaviour of metal-SiO2—GaAs structure characteristics by electrical equivalent circuit with constant phase element." Thin Solid Films 415.1-2 (2002): 133-137.
Kreuzer, M. et al. Development of an Immunosensor for the Determination of Allergy Antibody (IgE) in Blood Samples. Anal. Chim. Acta 2001, 442 (1), 45-53.
La Belle JT. Method for fabrication and verification of conjugated nanoparticle-antibody tuning elements for multiplexed electrochemical biosensors. Methods. 2013. 61:39-51. DOI: 10.1016/j.ymeth.2013.04.015.
La Belle JT et al. Development of a Novel Single Sensor Multiplexed Marker Assay. Analyst 2011, 136 (7), 1496-1501.
La Rosa, M. et al. Allergic Conjunctivitis: A Comprehensive Review of the Literature. Ital. J. Pediatr. 2013, 39 (1), 18.
Lemp, M. A. et al. Tear Osmolarity in the Diagnosis and Management of Dry Eye Disease. Am. J. Ophthalmol. 2011, 151 (5), 792-798.
Leonardi, A., et al. "Ocular allergy: recognizing and diagnosing hypersensitivity disorders of the ocular surface." Allergy 67.11 (2012): 1327-1337.
Lin, C. et al. Feasibility in the Development of a Multi-Marker Detection Platform. Biosens. Bioelectron. 2017. First available Oct. 2016.
Lin, C. J Biosens Bioelectron 2016, 7:3 (Suppl). Title: "Development toward a multi-marker and label-free platform sensor technology using electrochemical impedance spectroscopy and nanomaterials". Jun. 2016 vol. 7, Issue 3 ISSN: 2155-6210. Journal of Biosensors & Bioelectronics Http://dx.doi.org/10.4172/2155-6210.C1.030.
Lin, C.-E., 2015. Towards the Development of a Dry Eye Point of Care Diagnostic. Poster P-TH-159 presented at BMES 2015.
Lu, Y., et al. "Impedance spectroscopy analysis of human odorant binding proteins immobilized on nanopore arrays for biochemical detection." Biosensors and Bioelectronics 79 (2016): 251-257.
Lu, Y., et al. "Olfactory biosensor using odorant-binding proteins from honeybee: Ligands of floral odors and pheromones detection by electrochemical impedance." Sensors and Actuators B: Chemical 193 (2014): 420-427.
Mahato DK et al. Impedance, scaling behavior and conduction mechanism in double perovskite Pr2CuZr06 ceramic. J. Mater Sci: Mater Electron. 2016. 27:3845-3853. DOI: 10.1007/s10854-015-4232-4.
Makaraviciute, A. et al. Site-Directed Antibody Immobilization Techniques for Immunosensors. Biosens. Bioelectron. 2013, 50, 460-471.
Manaviat, M. R. et al. Prevalence of Dry Eye Syndrome and Diabetic Retinopathy in Type 2 Diabetic Patients. BMC Ophthalmol. 2008, 8 (1), 10.
Marques, M. R. et al. Simulated Biological Fluids with Possible Application in Dissolution Testing. Dissolution Technol 2011, 18 (3), 15-28.
Mattos, A. et al. A Dual Quartz Crystal Microbalance for Human Cardiac Troponin T in Real Time Detection. Sens. Actuators B Chem. 2012, 161 (1), 439-446.
Miller, Y. I. et al. Kinetics of Hemin Distribution in Plasma Reveals Its Role in Lipoprotein Oxidation. Biochim. Biophys. Acta BBA-Mol. Basis Dis. 1999, 1454 (2), 153-164.
Nandakumar, V., et al. "A low-cost electrochemical biosensor for rapid bacterial detection." IEEE Sensors Journal 11.1 (2011): 210-216.
Nomura, K., et al. "Tear IgE concentrations in allergic conjunctivitis." Eye 12.2 (1998): 296-298.
Ohashi, Y., et al. "Abnormal protein profiles in tears with dry eye syndrome." American journal of ophthalmology 136.2 (2003): 291-299.
Olokoba, A. B. et al. Type 2 Diabetes Mellitus: A Review of Current Trends. Oman Med. J. 2012, 27 (4), 269-273.
Olson, W. C. et al. Dissociation Kinetics of Antigen-Antibody Interactions: Studies on a Panel of Anti-Albumin Monoclonal Antibodies. Mol. Immunol. 1989, 26 (2), 129-136.
Ozcan, B. et al. Introducing a New Method for Evaluation of the Interaction between an Antigen and an Antibody: Single Frequency Impedance Analysis for Biosensing Systems. Talanta 2014, 125, 7-13.
Pandolfi, M. et al. A Histochemical Study of the Fibrinolytic Activity: Cornea, Conjunctiva, and Lacrimal Gland. Arch. Ophthalmol. 1967, 77 (2), 258-264.
Patil, A. V. et al. Immittance Electroanalysis in Diagnostics. Anal. Chem. 2015, 87 (2), 944-950.
Posa, A. et al. Schirmer Strip vs. Capillary Tube Method: Non-Invasive Methods of Obtaining Proteins from Tear Fluid. Ann. Anat.-Anat. Anz. 2013, 195 (2), 137-142.
Rinaldi Al et al. Impedimetric non-enzymatic glucose sensor based on nickel hydroxide thin film onto gold electrode. Sensors and Actuators B: Chemical. 2016. 228:43-52.
Ronkainen, N. J., et al. "Electrochemical biosensors." Chemical Society Reviews 39.5 (2010): 1747-1763.
Rosario, N. et al. Epidemiology of Allergic Conjunctivitis. Curr. Opin. Allergy Clin. Immunol. 2011, 11 (5), 471-476.
Roy, N. S. et al. The Growing Need for Validated Biomarkers and Endpoints for Dry Eye Clinical ResearchBiomarkers and Endpoints in Dry Eye Clinical Research. Invest. Ophthalmol. Vis. Sci. Apr. 2017, 58 (6), BIO1-BIO19.
Small, D. et al. Comparison of Tear Sampling Techniques for Pharmacokinetic Analysis: Ofloxacin Concentrations in Rabbit Tears after Sampling with Schirmer Tear Strips, Capillary Tubes, or Surgical Sponges. J. Ocul. Pharmacol. Ther. 2000, 16 (5), 439-446.
Stengel, M., et al. "Electric displacement as the fundamental variable in electronic-structure calculations." Nature Physics 5.4 (2009): 304-308.
Stull, C. et al. The Prevalence and Characteristics of Chronic Ocular Itch: A Cross-Sectional Survey. Itch 2017, 2 (1), e4. Published online Mar. 24, 2017.
Su, X. et al. Self-Assembled Monolayer-Based Piezoelectric Crystal Immunosensor for the Quantification of Total Human Immunoglobulin E. Anal. Biochem. 1999, 273 (1), 66-72.
Sullivan, S.D., et al. "Cost-effectiveness of risk stratification for preventing type 2 diabetes using a multi-marker diabetes risk score." Journal of medical economics 14.5 (2011): 609-616.

(56) References Cited

OTHER PUBLICATIONS

Van Berkel, P. H. et al. Characterization of Monoclonal Antibodies against Human Lactoferrin. J. Immunol. Methods 2002, 267 (2), 139-150.
Van Setten, G.-B. et al. Effects of the Schirmer Test on the Fibrinolytic System in the Tear Fluid. Exp. Eye Res. 1990, 50 (2), 135-141.
Wang, J. (2006). Electrochemical biosensors: towards point-of-care cancer diagnostics. Biosensors and Bioelectronics, 21(10), 1887-1892.
Wang, T. J. et al. (2006). Multiple biomarkers for the prediction of first major cardiovascular events and death. New England Journal of Medicine, 355(25), 2631-2639.
Ang, T. J. et al. (2007). Multiple biomarkers and the risk of incident hypertension. Hypertension, 49(3), 432-438.
Wiesner, A. (2004). Detection of tumor markers with ProteinChip technology. Current pharmaceutical biotechnology, 5(1), 45-67.
Xiao, Y. et al. Enzyme-Linked Immunosorbent Assay (ELISA) and Blocking with Bovine Serum Albumin (BSA)—not All BSAs Are Alike. J. Immunol. Methods 2012, 384 (1), 148-151.
Yang, Q. et al. (2012). Trends in cardiovascular health metrics and associations with all-cause and CVD mortality among US adults. Jama, 307(12), 1273-1283.
Yun, J, et al. "In-vivo biotissue discrimination using electrochemical impedance spectroscopy on a hypodermic needle with fine interdigitated electrodes." 2016 IEEE 29th International Conference on Micro Electro Mechanical Systems (MEMS). IEEE, 2016.
Zhou, L., et al. (2012). In-depth analysis of the human tear proteome. Journal of proteomics, 75(13), 3877-3885.

* cited by examiner

ANALYTE DETECTION USING ELECTROCHEMICAL IMPEDANCE SPECTROSCOPY-BASED IMAGINARY IMPEDANCE MEASUREMENT

CROSS REFERENCE TO RELATED APPLICATIONS

This application is a divisional of U.S. application Ser. No. 16/495,682, filed Sep. 19, 2019, which application is a U.S. National Stage of PCT Application No. PCT/US2018/023375 filed on Mar. 20, 2018, which claims the benefit of U.S. Provisional Patent Application No. 62/473,894, filed on Mar. 20, 2017, the entire contents of which are incorporated herein by reference.

FIELD OF THE INVENTION

This disclosure relates in general to single and multi-analyte (e.g., protein or lipid biomarker) detection through electrical impedance spectroscopy (EIS)-based imaginary impedance and in some embodiments to multi-analyte detection systems and methods involving imaginary impedance methods utilizing signal decoupling algorithms.

BACKGROUND

The development of multi-marker assays in place of single-marker assays is continuously rising as many studies have revealed the benefit of monitoring multiple analytes (e.g., biomarkers) in disease diagnosis, prognosis, and management. For example, in the case of diabetes mellitus, measuring insulin, glucose, and glucagon provides a more comprehensive understanding of a patient's state of health than glucose alone, which then provides more accurate information for insulin administration.

Currently, one of the most common mechanisms for multi-marker detection employs multi-sensor arrays, but detecting multiple anyalytes using a single electrochemical sensor has not yet been demonstrated.

SUMMARY

Embodiments herein relate to a label-free, single-sensor detection of one or more analytes using electrochemical impedance spectroscopy (EIS), imaginary impedance, and signal decoupling programing and methods. This is believed to be the first report of using imaginary impedance for analyte detection and multi-marker detection.

Thus, methods are disclosed for detecting one or more analytes in a sample utilizing Electrochemical Impedance Spectroscopy (EIS)-based imaginary impedance measurement that include comparing an imaginary impedance measurement to a calibration curve of concentrations for each target analyte. In some embodiments, the calibration curve of concentrations for each target analyte is established at an optimal frequency.

In other embodiments, a signal decoupling algorithm is utilized for detection of more than one analyte on an electrode.

These and other aspects are further disclosed in the accompanying written description and drawings.

DETAILED DESCRIPTION

Figure 1:
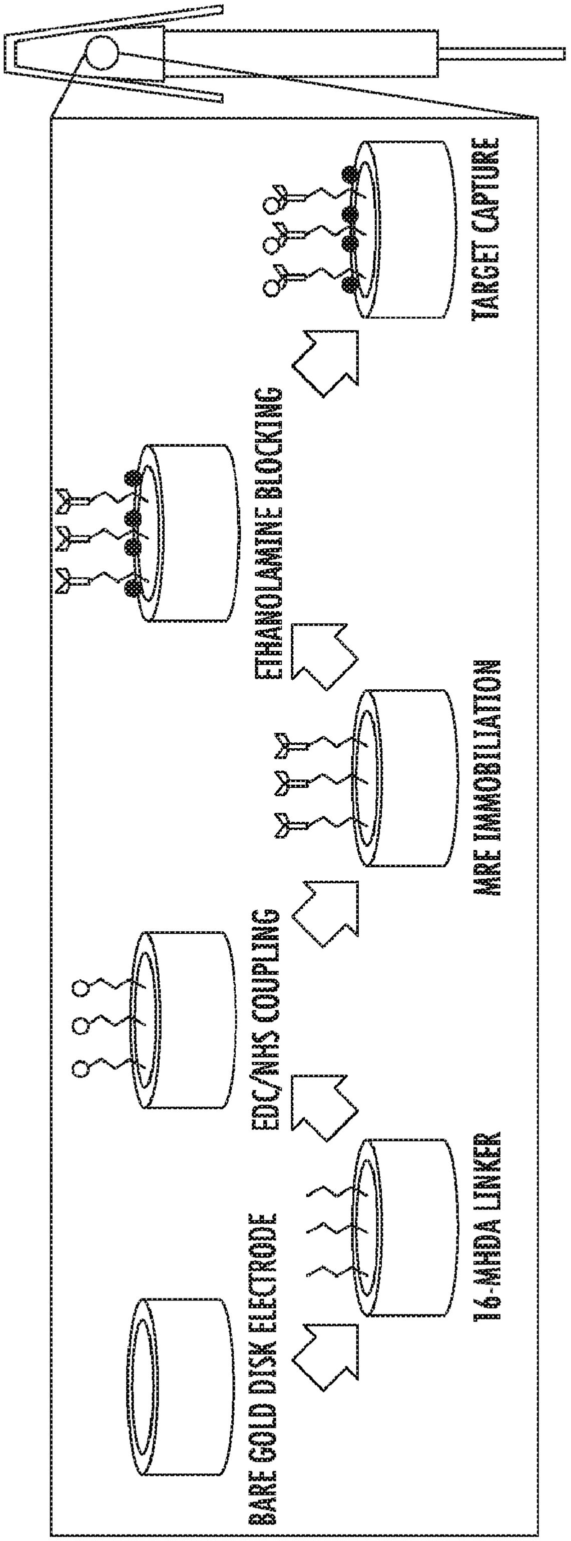
FIG. 1: Schematic of one embodiment of a sensor in terms of fabrication and setup.

Embodiments herein relate to apparatus, systems, and methods for detection of one or more analyte using electrochemical impedance spectroscopy (EIS), imaginary impedance, and signal decoupling techniques EIS has the potential for multi-marker detection. EIS offers various advantages for biosensing, including improved sensitivity, label-free detection and speed (<90 seconds)). It measures the resistance and capacitance of an electrochemical system with variable AC signal. The AC signal consists of a varying potential and a wide range AC frequency sweep. When varying AC signals are applied to the sample of interest, a current response is generated. The current response is measured over the range of frequencies encompassed by the sweep and is then used to calculate the real, imaginary, phase angle, and complex impedance. Mathematically, the complex impedance is defined by the equation below:

$$Z(j\omega) = \frac{U(j\omega)}{I(j\omega)} = Z_r(\omega) + jZ_i(\omega) \tag{1}$$

Where, $Z(j\omega)$ is the complex impedance, $\omega$ the angular frequency (which is equivalent to $2\pi f$ where f is the input frequency), $U(j\omega)$ the applied potential, $I(j\omega)$ the current response, $Z_r(\omega)$ the real impedance, and $jZ_i(\omega)$ the imaginary impedance.

After investigating the correlation between the complex impedance and target concentration, the concept of optimal frequency was developed. The optimal frequency of an analyte is the AC frequency at which the resulting impedance best represents the interaction between the biomarker and its MREs (Molecular Recognition Elements). The optimal frequency is determined by optimizing the responsivity and R-square values (RSQ). It offers an orthogonal means for target detection in addition to the specific interaction between target and their MREs. By determining the optimal frequencies of the biomarkers of interest, each biomarker may be detected at its optimal frequency simultaneously on a single sensor platform, giving rise to the possibility of a multi-marker detection platform technology.

However, using complex impedance to determine the optimal frequency and measure the target concentration of multiple biomarkers simultaneously has a major limitation: signal overlap. To address this issue, novel approaches to determine a biomarker's optimal frequency by using imaginary impedance have been developed. For example, one can correlate imaginary impedance to target concentrations and to determine optimal frequencies. Since imaginary impedance correlates to capacitance, a link may be made to optimal frequency in terms of effective capacitance and constant phase element.

Also developed are novel algorithms that decouple the convoluted signal when two or more biomarkers are co-immobilized onto a single sensor. As a verification, and in one example, an investigation of the feasibility of the approach to simultaneously detect LDL and HDL is demonstrated. These two lipoproteins are key biomarkers for coronary vascular disease (CVD), which is the leading cause of death in the United States with over 800,000 deaths per year. The National Cholesterol Education Program recommends the use of LDL and HDL as risk indicators for the development of CVD. Furthermore, the LDL/HDL ratio is an excellent predictor of coronary heart disease risk and an outstanding monitor for the effectiveness of lipid lowering therapies. Thus, a multi-marker sensor that can detect LDL and HDL simultaneously would greatly benefit the efficiency of diagnosing CVD and serve as a template to other multi-marker electrochemical sensors employing antibodies as MREs.

Non-Limiting Examples

The sensors used in this embodiment include gold disc electrodes (GDEs), silver/silver chloride reference electrodes, and platinum counter electrodes (CH Instrument, USA). The gold surface thickness of a GDE is approximately 2.5 mm. All EIS measurements were performed at room temperature using a CHI660C Electrochemical Analyzer from CH Instrument, USA. GDEs were polished with 100 figure-eight motions on Buehler felt pads using 3.0, 1.0, and 0.05 μm grit alumina oxide in distilled water (DI) followed by sonication in DI for 15 min. After sonication, the formal potential was obtained by performing cyclic voltammetry from −1.0 V to 1.0 V in a solution of 100 mM potassium ferricyanide prepared in pH 7.4 phosphate buffer saline (PBS). EIS was then performed using the formal potential and a 5 mV AC sine wave sweeping from 1 Hz to 100 kHz to measure the bare impedance of GDEs, which helps determine GDEs' surface topography.

After rinsing the GDEs with DI, 1 mM of 16-mercapto-hexadecanoic acid (16-MHDA) in ethanol was incubated onto the GDEs for 1 hr to form a self-assembly monolayer (SAM). Post-MHDA impedance was measured at the formal potential of each GDE for quality control. The carboxylate groups on the tail end of 16-MHDA were then activated by incubating the sensor with 40 mM 1-ethyl-3-(3-dimethyl-aminopropyl) carbodiimide (EDC) and 20 mM sulfo-derivative of N-hydroxysuccinimide (NHS) for 1 hr. After washing the sensor with DI, 5 mg/dL of the antibodies prepared in pH 7.4 PBS (LDL, HDL, or LDL and HDL combined) were then immobilized onto the sensor at room temperature for 1 hr. For LDL and HDL co-immobilization, the antibodies were pre-mixed at a 1:1 ratio and the final concentration of each antibody was 5 mg/dL. The sensors were then washed with PBS following the immobilization and the remaining reactive sites were blocked with 1% ethanolamine for 30 min. After rinsing the sensors with PBS, they were stored at 4° C. until further use.

The reagents and solvents, 16-MHDA, EDC, NHS, and potassium ferricyanide were all obtained from Sigma-Aldrich, USA. PBS was purchased from VWR International, USA. LDL and HDL specific antibodies (not to cholesterol) were purchased from Academy Biomedical Company, USA.

All sensors were brought to room temperature prior to testing. A Serial dilution made in PBS was used to prepare purified LDL and HDL samples. All samples were then well mixed with 100 mM potassium ferricyanide at a 1:1 ratio to form a total volume of 100 μL of each sample at 50, 10, 5, 1, 0.5, 0.1, 0.05, 0.01, and 0 mg/dL. For LDL and HDL co-immobilization testing, the two markers were well mixed at a 1:1 ratio in a similar manner and the mixture has the concentration of 0-10 mg/dL for each biomarker. EIS was performed to measure each sample's impedance at each sensor's formal potential from 1 Hz to 100 kHz at 12 points per decade. The impedance at each frequency was correlated to the applied biomarker concentrations and the results were used to calculate sensitivity (slope) and specificity (RSQ). The slope and RSQ values were then plotted against the frequency to determine the frequencies at which the biomarker can be best detected (the optimal frequency).

EIS typically outputs 4 parameters: the real impedance ($Z_r$), imaginary impedance ($Z_i$), phase angle (∅), and complex impedance (Z). Their relationships are shown below:

$$Z_r = |Z|\cos(\emptyset) \quad (2)$$

$$Z_i = |Z|\sin(\emptyset) \quad (3)$$

Where real impedance correlates to resistance and imaginary impedance capacitance and/or inductance. Nyquist plots are then plotted with real impedance ($Z_r$) on the x-axis and the negative of imaginary impedance ($-Z_i$) on the y-axis, producing a semi-circle curve shape. As targets enter the sensing area where MREs are immobilized, binding will occur and form the MRE-target complex. These complexes will obstruct the flow of electrons, causing a change in impedance that is concentration dependent.

Complex impedance encompasses everything in the system, such as the Warburg (diffusion) resistance, charge transfer resistance, solution resistance, and double layer capacitance. By correlating the complex impedance at each frequency to the target concentrations, a slope and RSQ can be obtained at each frequency. The slope and RSQ values were then plotted against the frequency from 1 Hz to 100 kHz. The frequency with best slope and RSQ trade off was deemed the optimal frequency of the biomarker. Calibration curves can then be generated by correlating the complex impedance to target concentrations at the optimal frequency.

Figure 2A:
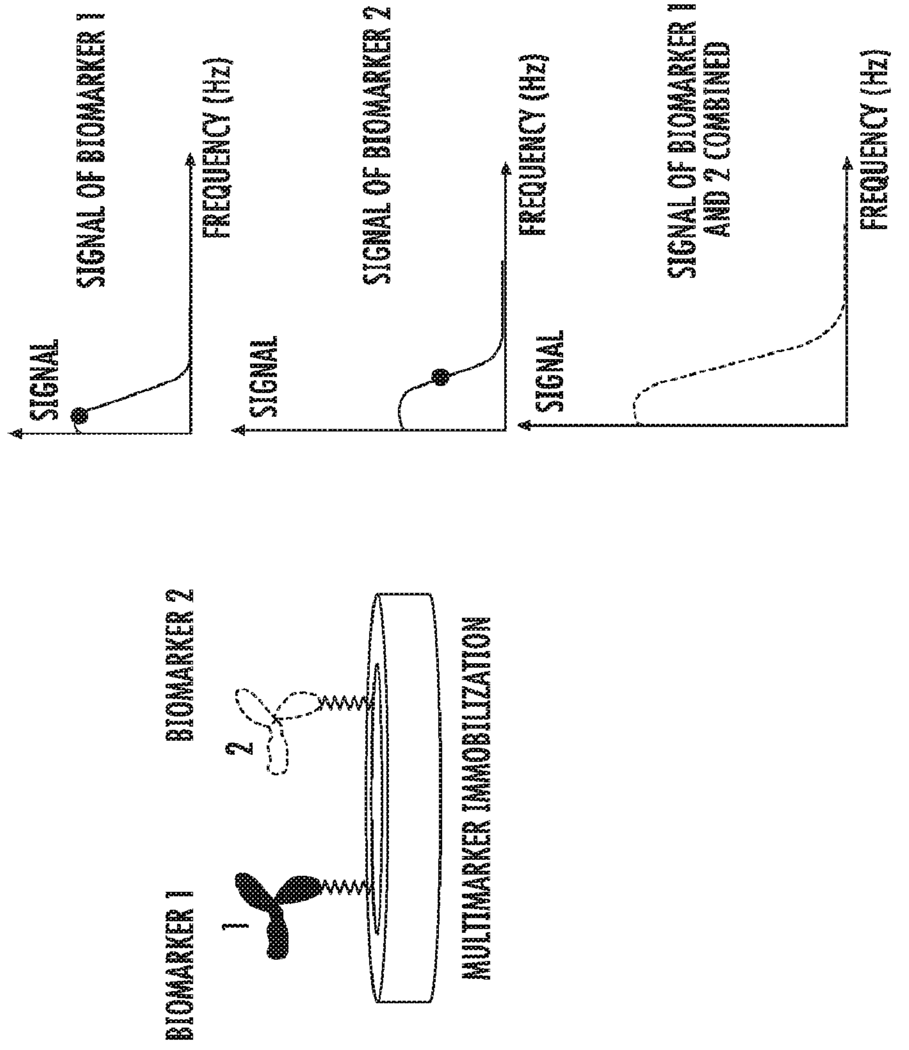
FIG. 2: Schematic representation of an embodiment of a multi-marker detection sensor, as well as two biomarker impedance signals and the predicted signal when co-immobilized on the same sensor. Each biomarker's optimal frequency is determined by sensitivity and RSQ using A) complex impedance and B) imaginary impedance. The black circle represents the optimal frequency of biomarker 1 and white circle the optimal frequency of biomarker 2 in each approach. Notice that in FIG. 2A, due to signal overlapping, the optimal frequencies of both markers are not distinguishable when co-immobilized.

Complex impedance across the frequency spectrum is typically highest at low frequencies (<1 k Hz) and lowest at high frequencies (FIG. 2A). While this is not an issue for single biomarker detection, the abundance of signal from one biomarker's optimal frequency can overlap with the signal from another biomarker's optimal frequency, posing a great challenge for multi-marker detection.

Figure 2B:
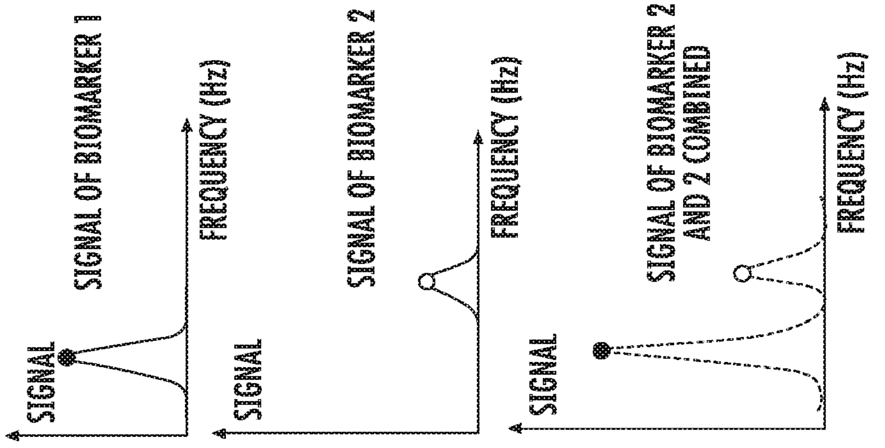

On the other hand, as illustrated in FIG. 2B, imaginary impedance offers an additional parameter for the determination of optimal frequency: peak location. In contrast to complex impedance, imaginary impedance peaks at a specific frequency, forming a parabolic shape when plotted across frequencies. By correlating the imaginary impedance to target concentration, slope and RSQ values can be obtained. When plotting the slope values over a range of frequencies, a parabolic pattern is obtained with a distinct peak often matching a high RSQ value. Optimal frequency can then be determined by locating the frequency at which the peak slope occurs. Calibration curves can then be calculated by correlating the imaginary impedance to target concentrations at the optimal frequency.

Briefly, using XL-fit, a Microsoft Excel add-on for parabolic fitting, the signals of purified LDL and HDL were first modeled and used to predict the co-immobilized signal. The raw co-immobilization data was then used to match against the predicted signal for signal decoupling.

All electrochemical circuit modeling was done via ZSimpWin (Echem Software, USA). EIS data was fit against potential electrochemical equivalent circuit models and evaluated using a Chi-square analysis and mean percent standard deviation (mean % stdev). The procedure was repeated to obtain the best fitting electrochemical equivalent circuit for purified LDL, purified HDL, and co-immobilized LDL and HDL.

Figure 3:
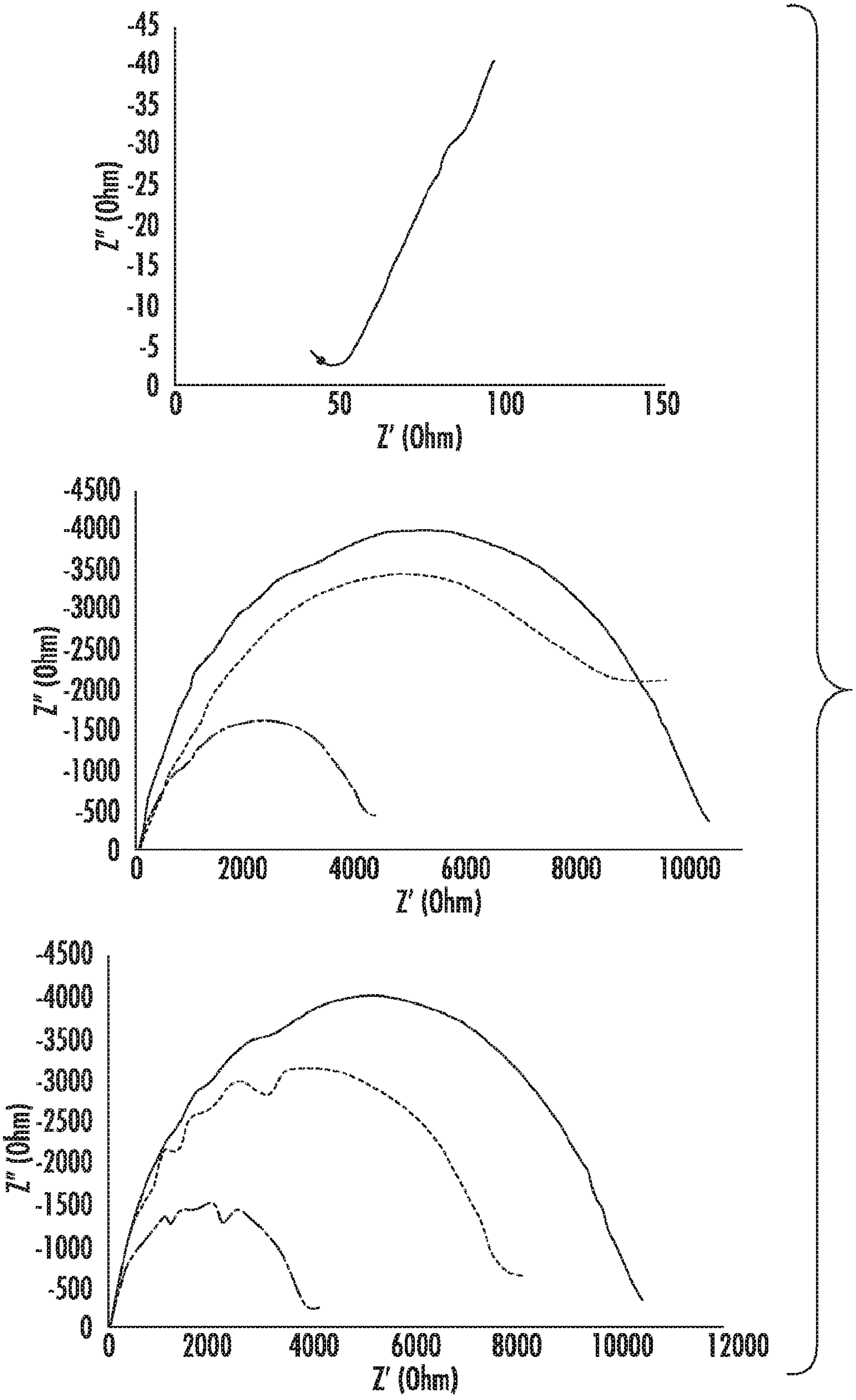
FIG. 3: Nyquist plots for bare gold disk electrode (left); 16-MHDA (solid line), blank (thick dashed line) and 10 mg/dL HDL (light dashed line) (center); and 16-MHDA (solid line), blank (thick dashed line) and 10 mg/dL HDL (light dashed line) (right).

For quality control, AC impedance measurement was performed 3 times throughout the sensor preparation process: after polishing the bare electrodes, after MHDA, and after blocking. As shown in FIG. 3*a*, a clean electrode showed only a Warburg tail, suggesting that the system is dominated by diffusion. Damaged or warped Gold Disk Electrodes (GDE's) will have much higher impedance after polishing. As shown in FIGS. 3*b* and 3*c*, the impedance will increase drastically after successful MHDA binding and decrease after successful immobilization of MREs. When targets were introduced to the sensors, the impedance increased significantly from the blank, suggesting successful binding. The specificity of binding and surface coverage were evaluated. Of note is that the bare electrode impedance values are a hundred times smaller than the impedance values when binding occurs, suggesting that the cables have negligible effects on the measurements.

Figure 4A:
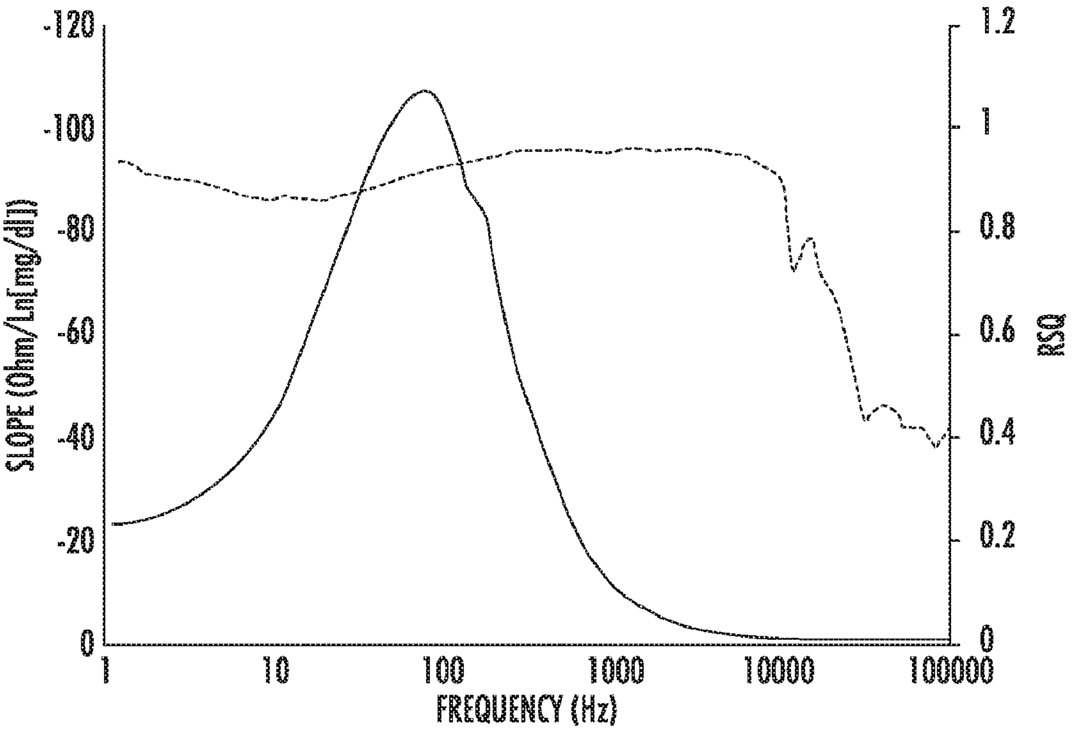
FIG. 4: Electrochemical characterization of LDL (black) and HDL (grey) in purified solution. The imaginary impedance slope is overlaid with RSQ (dashed line) across the frequency sweep for: (a) purified LDL and (b) purified HDL. The complex impedance slope is overlaid with RSQ across the frequency sweep for: (c) purified LDL and (d) purified HDL. Using the imaginary impedance approach, (e) shows the overlay of the LDL (black) and the HDL (grey) calibration curves at each marker's optimal frequency over the concentration range tested (0-50 mg/dL for both). The inset is a zoomed-in view of the HDL slope from 0 to 0.1 mg/dL.
Figure 4B:
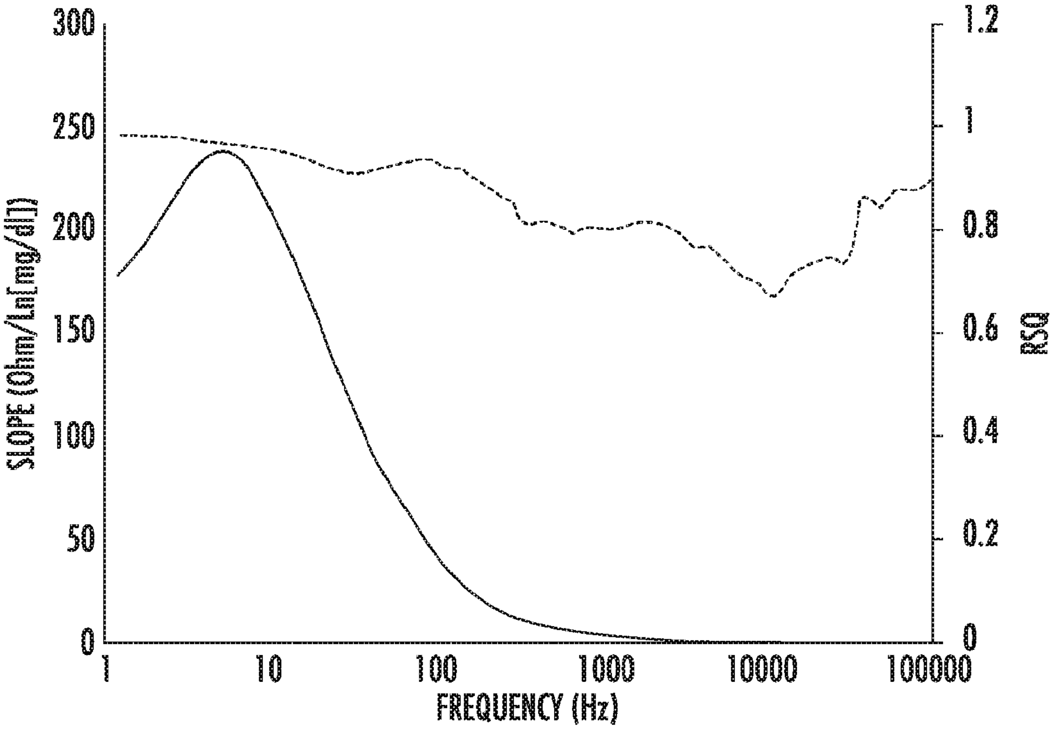

The EIS responses of LDL and HDL in imaginary impedance (FIGS. 4*a* and 4*b*) exhibit distinct peaks at various frequencies, resembling a bandpass filter-like shape. In contrast, the complex impedance (FIGS. 4*c* and 4*d*) does not exhibit the distinct peaks and resembles a shape like a low-pass filter. The optimal frequency was calculated by choosing the frequency with highest slope and satisfactory RSQ (>0.85). Using the imaginary impedance approach, the optimal frequencies of LDL and HDL were found to be at 81.38 Hz and 5.49 Hz, respectively (FIGS. 4*a* and 4*b*). Using the complex impedance approach, the optimal frequency of HDL could be found at 1.18 Hz. However, the optimal frequency for LDL could range from 1.18 Hz to 37.56 Hz as the tradeoffs between slope and RSQ are difficult to evaluate.

Figure 4C:
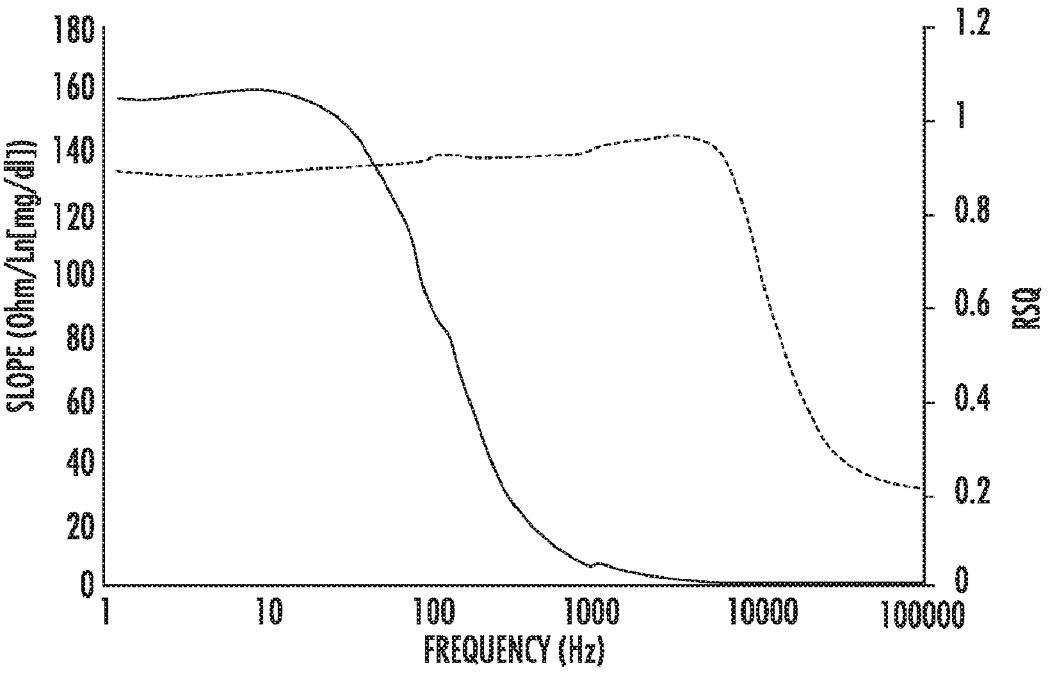
Figure 4D:
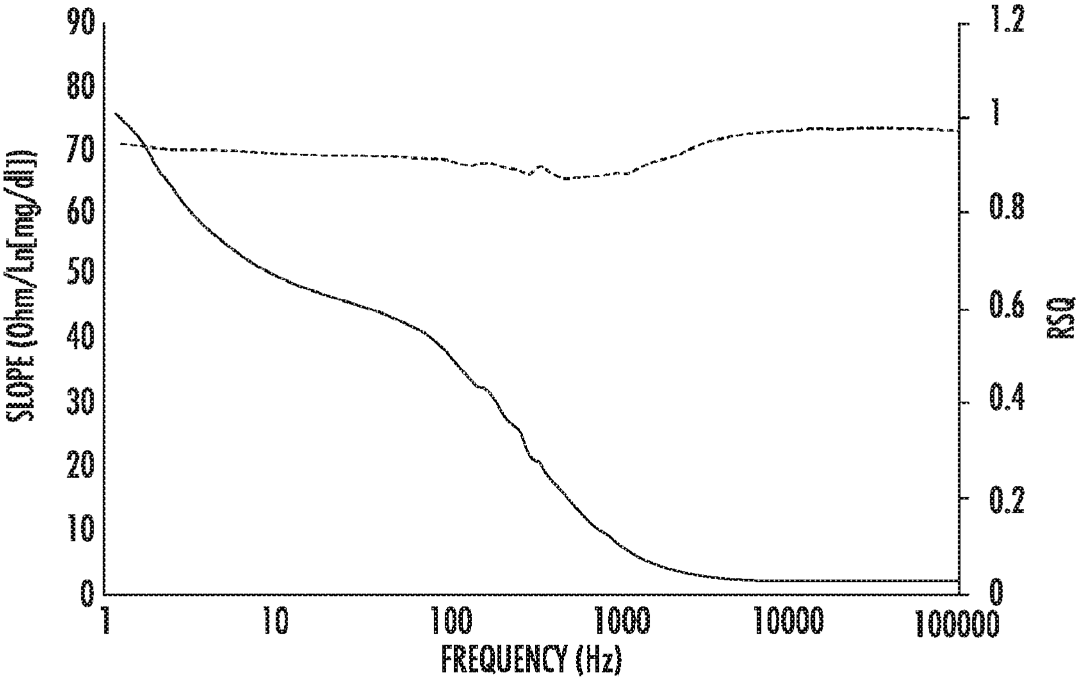
Figure 4E:
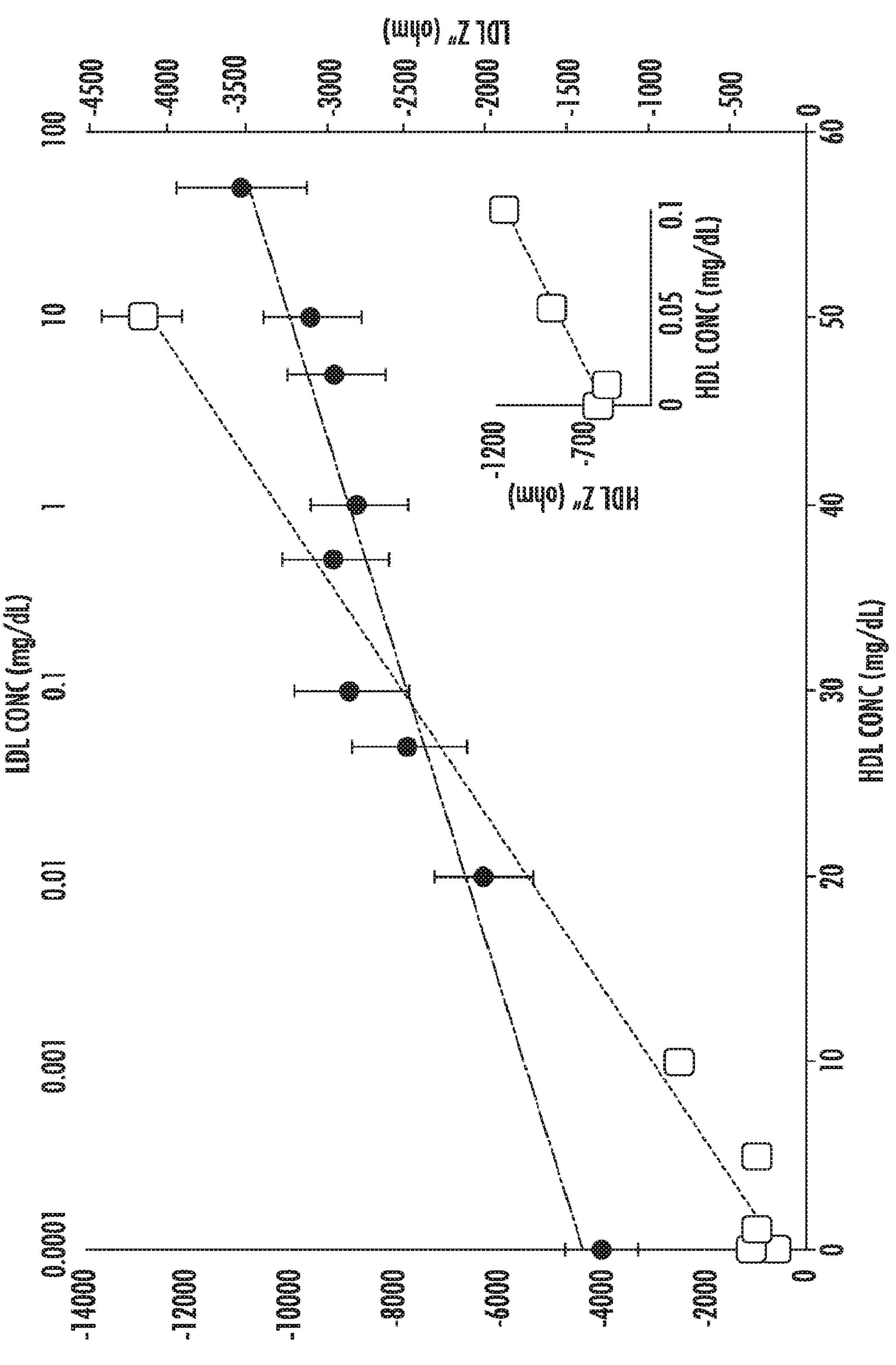

Using the imaginary impedance approach, the calibration curve at each biomarker's optimal frequency was attained by graphing the concentration versus output imaginary impedance and fitted to a regression line. The calibration curve for LDL at an optimal frequency of 81.48 Hz is described as y=−106.7 ln(x)−2881.5 (FIG. 4*e*, black curve) with an RSQ of 0.92. The calibration curve for HDL at an optimal frequency of 5.49 Hz is described as y=−238.16x−783.11 with an RSQ of 0.97 (FIG. 4*e*, grey curve). The dynamic ranges for LDL and HDL sensors are 35.78 mg/dL-211.22 mg/dL and 42.43 mg/dL-172.65 mg/dL, respectively, with both encompassing the clinically relevant range of 100-190 mg/dL and 40-60 mg/dL, respectively. Of note is that LDL was found to have a logarithmic fit while HDL a linear fit. The association and disassociation rate constants for LDL are 342 $nM^{-1}\cdot min^{-1}$ and 27 $min^{-1}$, respectively, and HDL 90 $nM^{-1}\cdot min^{-1}$ and 3 $min^{-1}$, respectively.

Figure 5A:
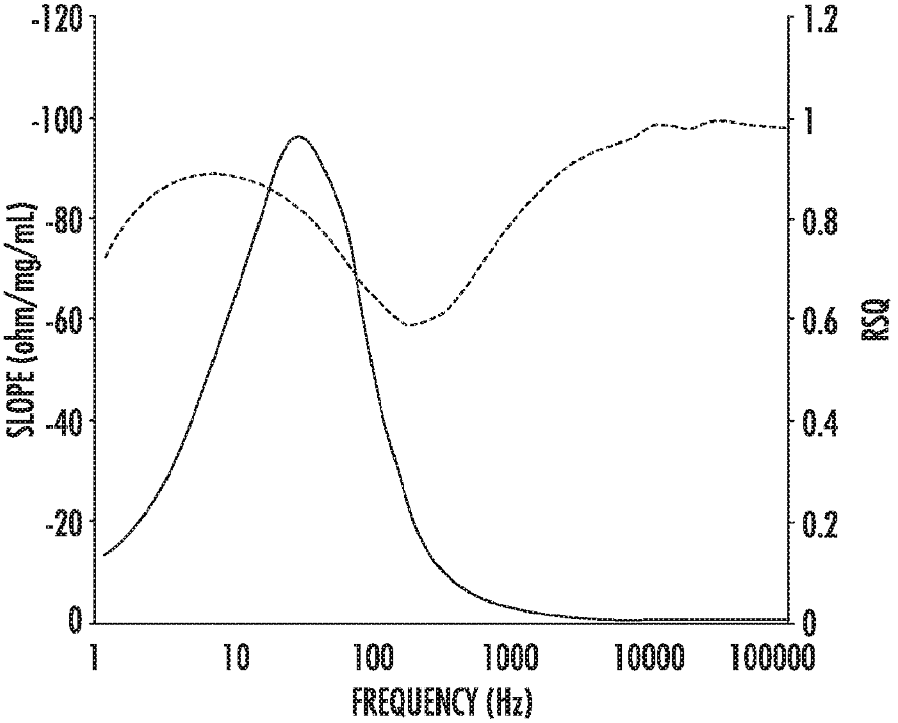
FIG. 5: Co-immobilization of HDL and LDL. (a) raw data plotting the slope (solid line) and RSQ (dashed line) across frequency sweep, with a unique peak at 31.5 Hz; (b) The decoupled signal using the described algorithm. The two peaks occur at 3.74 Hz and 175.8 Hz, with each representing the optimal frequency of HDL and LDL, respectively. The RSQ also peaks at these frequency locations; (c) The comparison of the predicted HDL values using the calibration curve, versus the actual input values. (d) The comparison of the predicted LDL values using the calibration curve, versus the actual values.
Figure 5B:
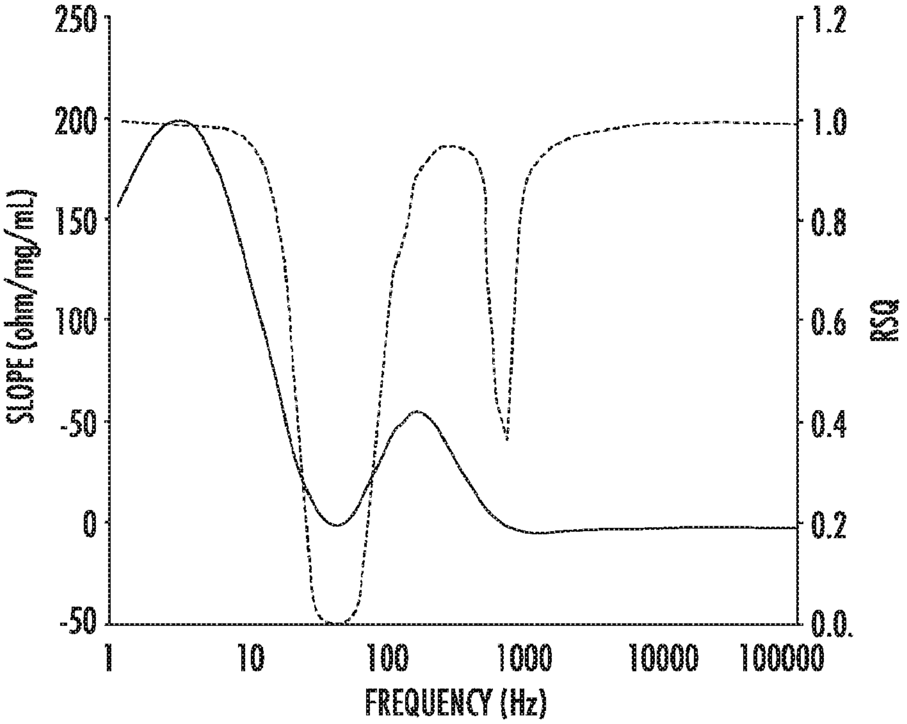
Figure 5C:
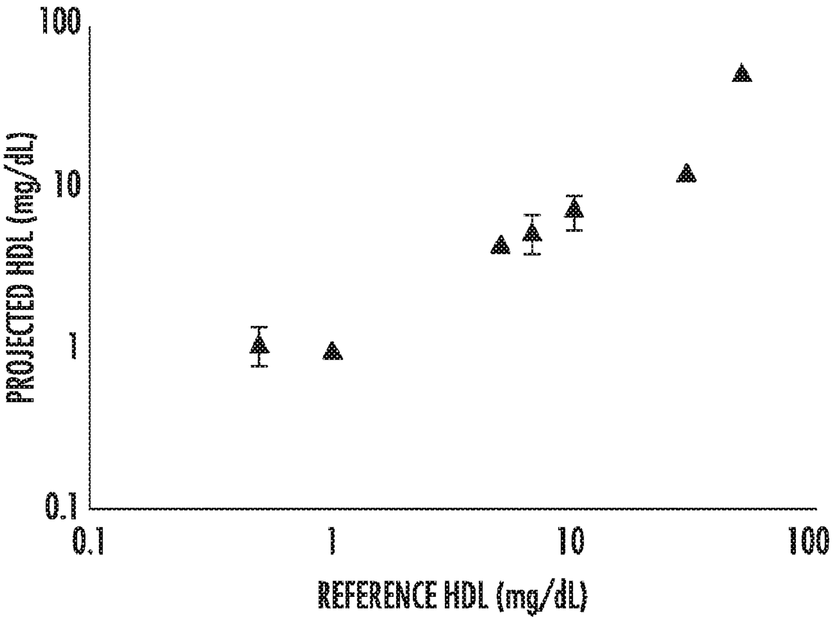
Figure 5D:
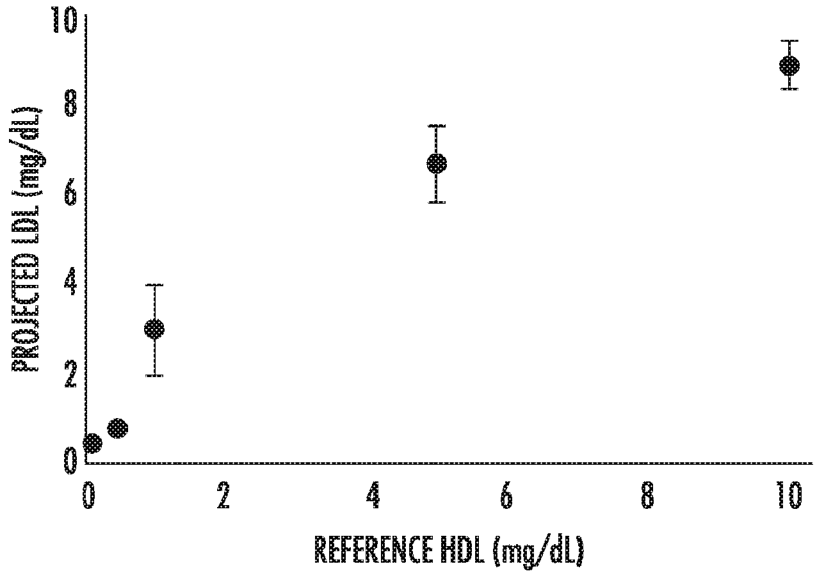

The co-immobilized impedance signal of LDL and HDL shows a similar bandpass filter shaped peak at 31.5 Hz with a strong correlation. Knowing that the peaks in purified LDL and HDL are 81.38 Hz and 5.49 Hz, respectively (FIGS. 4*a* and 4*b*), the summation of the two signals when co-immobilized can theoretically yield a single peak that is within the two frequencies. Note that the RSQ value of 1 with little to no slope at frequencies above 10 kHz shows the lack of signal above 10 kHz. Once the signal was decoupled using the algorithm described above, two peaks became apparent (FIG. 5*b*). The decoupled HDL peak shifted slightly from 5.74 Hz to 3.74 Hz with a slope of 199.4 ohm/(mg/dL), and correlation of 0.99. The decoupled LDL peak shifted from 81.38 Hz in purified to 175.8 Hz with a slope of 57.15 ohm/(mg/dL) and a correlation of 0.88. The slopes were then used to generate new calibration curves that can back-calculate the LDL and HDL concentrations. The results were then plotted against the reference concentrations (FIGS. 5*c*, 5*d*) for verification. The lower limit of detection for the multi-marker sensor is 1 mg/dL but upper limit of detection still requires further optimization. Note that FIGS. 5*c* and 5*d*'s scale bars have been adjusted to show only the linear range of the decoupled signal.

Figures 6A, 6B, 6C:
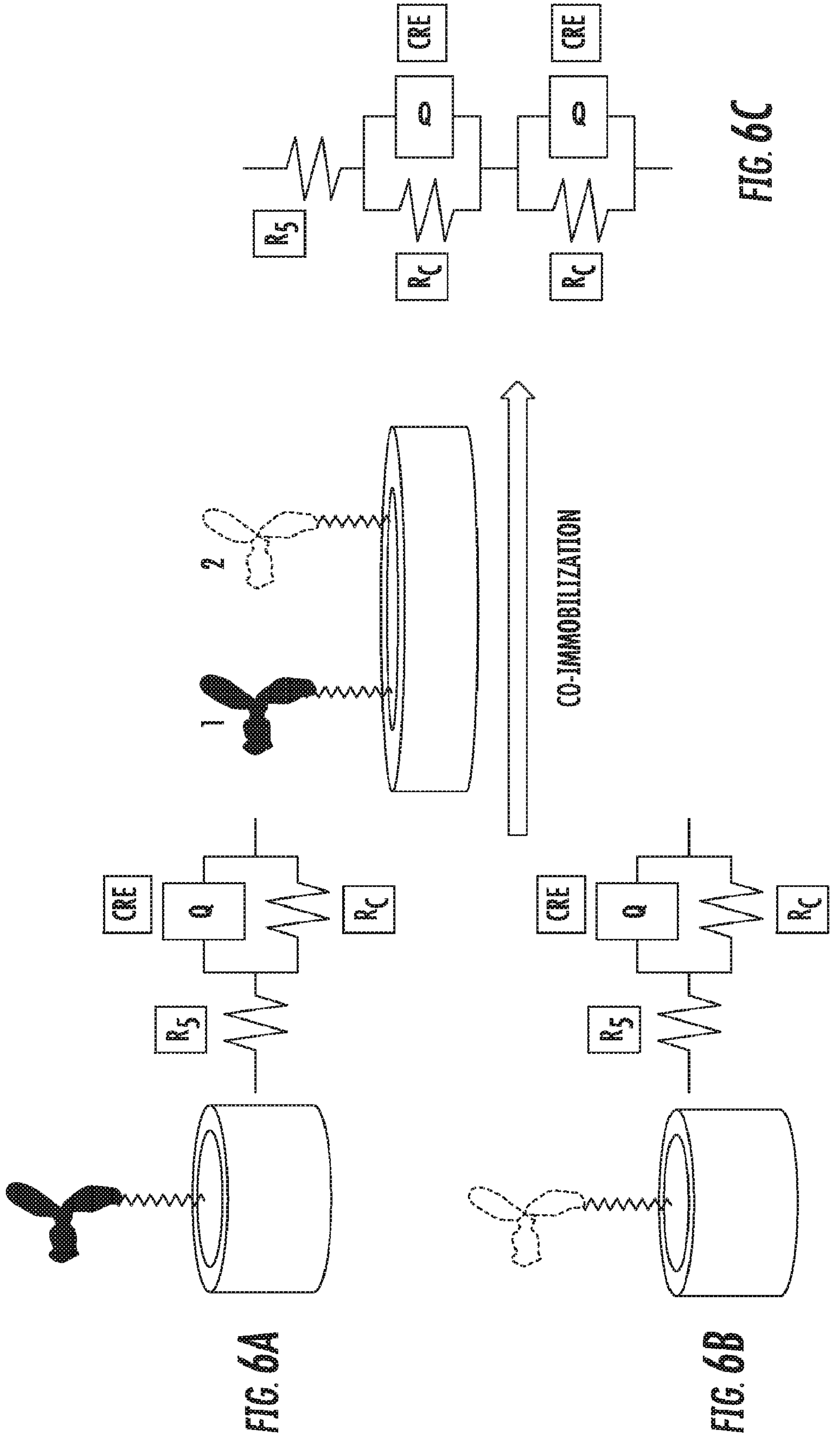
FIG. 6. Electrochemical equivalent circuits for purified LDL (A), HDL (B), and co-immobilized LDL and HDL (C). ($R_s$)=solution resistance; ($R_c$)=a combined resistance of charge transfer resistance ($R_{ct}$) and Warburg impedance (W); (Q)=constant phase element (CPE).

The electrochemical equivalent circuits for LDL and HDL were both found to be the R(QR) circuit, which can be considered a modified Randle's circuit ($R_s(Q[R_{ct}W])$ (FIG. 6). This modeling is consistent with the theory that electrical properties of proteins can be considered as a resistance-capacitance parallel circuit. The CPE represents an imperfect double layer capacitor consisting of the electrode, the SAM, MREs, and bound target molecules. The impedance of CPE ($Z_{CPE}$) is described as:

$$Z_{CPE} = \frac{1}{Q(j\omega)^n} \quad (4)$$

Where, $$j = (-1)^{1/2},\ \omega = 2\pi f$$

with f being the frequency of the applied AC potential, and n representing a fractional value between 0 to 1, with 0 describing a pure resistor and 1 an ideal double layer capacitor. The values of individual components in LDL's equivalent circuit are: $R_s$=239 ohms, Q=1.66E-7 $Ssec^n/cm^2$, n=0.87, $R_c$=21701 ohms. The values for HDL's equivalent circuits are: $R_s$=211 ohms, Q=6.69E-7 $Ssec^n/cm^2$, n=0.8, $R_c$=30015 ohms.

The equivalent circuit model of co-immobilized LDL and HDL was found to be a combination of individual LDL and HDL equivalent circuits: R(QR)(QR). While it is possible to model the co-immobilized LDL and HDL with the same R(QR) circuit, the chi-square and mean % stdev of R(QR)(QR) circuit (4.97E-04 and 2.01%, respectively) are much smaller than that of R(QR) circuit (1.49E-03 and 3.85%, respectively), suggesting a much better fit. The values for co-immobilization's equivalent circuits are: $R_s$=101 ohms, $Q_1$=1.73E-4 $Ssec^n/cm^2$, m=0.6, $R_{c1}$=7966 ohms, $Q_2$=2.07E-7 4 $Ssec^n/cm^2$, $n_1$=0.8, $R_{c2}$=9673 ohms.

The greatest challenge of measuring two biomarkers using a single co-immobilized sensor is the large amount of signal aliasing. As seen in FIGS. 4*c* and 4*d*, using the complex impedance approach can pose a great challenge for signal decoupling and back-calculation of target concentrations when applied in multi-marker detection settings. However, with the distinct peaks and higher RSQ values obtained using the imaginary impedance approach, individual signals are easily distinguished. The peak also makes determining optimal frequency much easier than in the complex impedance approach, i.e., using just the imaginary impedance allows researchers to focus on the capacitive signal resulting from the conformational changes of target-MRE binding.

By using decoupling algorithms, it is possible to detect two biomarker simultaneously on the same sensor. As disclosed herein, embodiments having an electrode operably configured to provide an EIS-based imaginary impedance measurement include computer processing components and capabilities utilizing non-transitory computer readable media having decoupling algorithm programing.

In one embodiment, to decouple the signal generated from two biomarkers (e.g., LDL and HDL) co-immobilized onto the same sensor surface, a unique decoupling algorithm is applied ae described below. All impedance values are imaginary impedance unless stated otherwise. Generally the calibration curve at each frequency is typically expressed in the form of:

$$y(f)=m(f)*x+b(f) \quad \text{(a)}$$

Where y is the imaginary impedance, m is the slope, x is the target concentration, f is the frequency, and b is the intercept. The term b(f) can be interpreted as a baseline adjustment value, which can vary in different sensor configurations and surface topography's. The slope, m(f), can be considered as the main signal generated from the binding of target molecules to their MREs including the association and disassociation rates.

Using this concept, it can be argued that LDL-HDL co-immobilized data has three components: the resulting imaginary impedance (y(f)), the impedance signal resulted from LDL and HDL (m(f)*x), and the baseline adjustment impedance (b(f)).

$$y_{1,2}(f)=m_{1,2}(f)*x_{1,2}+b_{1,2}(f) \quad \text{(b)}$$

Where 1 denotes LDL and 2 denotes HDL. If the pattern of b(f) in the HDL-LDL co-immobilized setup can be modeled, then the impedance values caused by b can be subtracted from the overall co-immobilized impedance values. The remaining impedance values across all frequencies are then the decoupled impedance values resulted from the binding of the LDL and HDL molecules to their corresponding antibodies.

For ease of modeling, the concentrations of LDL and HDL antibodies are both 50 µg/mL and are co-immobilized onto the gold sensor at a 1:1 ratio. XLfit, a Microsoft Excel add-on for parabolic fitting, was used to model the parabolic curves that were generated from plotting imaginary impedance (y(f)) against frequencies and slopes (m(f)) against frequencies. The parabolic fitting was performed on both purified LDL and HDL to model their electrochemical responses ($m_1$(f) and $m_2$(f)). The projected impedance values ($y'_1$(f) and $y'_2$(f)) without the adjustment values ($b_1$(f) and $b_2$(f)) were then obtained by multiplying the parabolic fitting of HDL and LDL slopes ($m_1$(f) and $m_2$(f)) with their target concentrations ($x_1$ and $x_2$). The projected impedance values of LDL and HDL ($y'_1$(f) and $y'_2$(f)) were then added together to project the impedance values of co-immobilized LDL and HDL ($y'_{1,2}$(f)) without the adjustment values ($b_{1,2}$(f)). The adjustment values ($b_{1,2}$(f)) were then obtained by subtracting the predicted co-immobilized impedance values ($y'_{1,2}$(f)) from the actual co-immobilized impedance values ($y_{1,2}$(f)).

After modeling the adjustment values ($b_{1,2}$(f)), the projected adjustment values ($b'_{1,2}$(f)) at each frequency can be obtained. Lastly, by subtracting the projected adjustment values ($b'_{1,2}$(f)) from the actual co-immobilized impedance values ($y_{1,2}$(f)), the decoupled impedance values resulted from only the binding of LDL and HDL could be obtained. New calibration curves for each biomarker where then obtained to detect LDL and HDL separately.

Based on these unique characteristics, the imaginary impedance approach better suits the characterization of multi-marker detection, while the complex impedance approach is more specific to single-marker detection.

The idea of optimal frequency is to provide an orthogonal means (in addition to the binding of target to MRE) for measuring target molecules. Although the optimal frequency of a biomarker appears to have a characteristic signal peak at which the impedance response is highest, it is different from the concept of absorbance spectroscopy. Rather, we hypothesized that the optimal frequency be interpreted as the AC input frequency at which the displacement field and electron transferring of the whole system best correlates to the target's binding phenomenon.

Looking at the system geometry and the results of the electrochemical circuit modeling, an imperfect parallel plate capacitor (IPPC) is used to model the interaction of chemical and biological molecules. The surface of the sensor is considered as the bottom plate. The molecular recognition elements and the bounded target molecules at the end of the SAM are considered as the top plate of the capacitor. The length of SAM chains determine the distance between the two parallel plate capacitors. While the bottom plate is relatively smooth, the top plate, depending on the orientation of the MREs and the binding of target molecules, can report varying degrees of surface roughness.

When EIS's varying potential (E(ω)) is applied, a displacement current can pass through the IPPC. The displacement current flows because of the electric displacement field (D), which is a vector accounting the effects of free and bound charge inside the medium. The electric displacement field can be modeled as:

$$D(\omega)=\varepsilon(\omega)*E(\omega) \quad (5)$$

It should be recalled that the impedance relates to how the electrons can flow from the top of the medium to the sensor surface. With the IPPC, the concept of relative permittivity ($\varepsilon_r(\omega)$) can be employed:

$$\varepsilon_r(\omega) = \frac{\varepsilon(\omega)}{\varepsilon_0} \tag{6}$$

Where $\varepsilon_0$ is the permittivity of the medium in a vacuum, $\varepsilon(\omega)$ the absolute permittivity of the medium, and $\omega$ the angular frequency. The resulting capacitance ($C(\omega)$) and impedance ($Z(\omega_c)$) of the imperfect parallel plate capacitor thus becomes:

$$C(\omega) = \frac{\varepsilon_r(\omega) * A * k}{d} \tag{7}$$

$$Z(\omega)_c = \frac{1}{j\omega C(\omega)} \tag{8}$$

Where A is the surface area of the parallel plates, k the dielectric constant of the material, and d the distance between the parallel plates. The term effective capacitance ($C_{eff}$) is then related to CPE, derived from:

$$C_{eff} = Q^{\frac{1}{n}} * \left(\frac{R_s R_c}{R_s + R_c}\right)^{\frac{1-n}{n}} \tag{9}$$

In summary, as AC voltage is applied, the charges of ions and the molecules can be polarized by the displacement field $D(\omega)$, influencing the effective capacitance, which can be related to the constant phase element, Q. The optimal frequency can thus be interpreted as the frequency of an input AC voltage at which the resulting displacement field, the relative permittivity, and the capacitance of the IPPC best correlate to the binding of the target to its MRE. The imaginary impedance, which correlates to the capacitance, can thus be correlated to target concentrations.

LDL is approximately 22 nm to 27.5 nm in diameter and HDL 7.3-13 nm. Given that, it is interesting to note that LDL was detected at a higher frequency (81.38 Hz) and HDL at a lower frequency (5.49 Hz) in purified solution (FIGS. 4*a* and 4*b*), suggesting a potential relationship between optimal frequency and molecular size. Targets with various sizes can bind to their MREs to form size varying complexes, affecting the capacitance of the IPPC and consequently the optimal frequencies. The association and disassociation rates of HDL (342 $nM^{-1} \cdot min^{-1}$ and 27 $min^{-1}$) are also much higher than that of LDL (90 $nM^{-1} \cdot min^{-1}$ and 3 $min^{-1}$), suggestion potential connection to optimal frequencies as well.

This phenomenon helps explain the shift in frequencies after co-immobilizing the two biomarkers. After co-immobilization the optimal frequencies of LDL and HDL (5.48 Hz and 81.38 Hz, respectively) shifted to 3.74 Hz and 175.8 Hz, respectively. Note that the CHI660C is only capable of measuring 12 frequencies per decade and 81.38 Hz is 4 data points away from 175.8 Hz, suggesting a higher resolution might be desirable for future investigation. Parameters that may have influenced the shift in optimal frequencies are steric hindrance, molecular diffusion rates, as well as orientation and shape of the MRE-target complex. Other factors such as binding kinetics; the association and dissociation rates; the physical changes that occur during binding; and whether the mechanism is 1 step or multistep process can all have impacts as well. These factors can affect the electron transfer rate and the capacitance of the IPPC despite the immobilization of the two markers' antibodies at a 1-to-1 ratio.

While EIS has been previously reported to have the theoretical capability of multi-marker detection on a single sensor, one of the major roadblocks to a successful multi-marker sensor has been the signal overlapping and decoupling. Here the inventors disclose multi-marker detection by detecting LDL and HDL simultaneously on GDEs. The inventors further disclose novel signal analyzing methods using just imaginary impedance, a signal decoupling algorithm, and discuss factors that may affect optimal frequencies.

The embodiments, methods, and examples described herein are illustrative and not meant to restrict the scope of the claims.

We claim:

1. A method for detecting binding of two or more target analytes in a sample utilizing Electrochemical Impedance Spectroscopy (EIS), comprising:

contacting an electrode with said sample, wherein said electrode includes two or more different analyte-capturing molecules immobilized thereto, wherein each of the two or more different analyte-capturing molecules is capable of specifically binding to one of the two or more target analytes;

exciting said electrode with an electrical signal having multiple different frequencies;

receiving a first imaginary impedance response signal from the electrode;

decoupling the first imaginary impedance response signal to generate a second imaginary impedance response signal that includes a first peak representing a first target analyte and a second peak representing a second target analyte;

detecting the first target analyte in said sample from the first peak in the second imaginary impedance response signal; and detecting the second target analyte in said sample from the second peak in the second imaginary impedance response signal.

2. The method of claim 1, further comprising comparing the second imaginary impedance response signal for each target analyte to a respective calibration curve of concentrations for each target analyte.

3. The method of claim 2, wherein said calibration curve of concentrations for each target analyte is established at an optimal frequency.

4. The method of claim 1, wherein the decoupling the first imaginary impedance response signal includes representing the first imaginary impedance response signal in the form of the following equation:

$$y_{1,2}(f) = m_{1,2}(f) * x_{1,2} + b_{1,2}(f),$$

wherein, sub-indices 1 and 2 respectively correspond to the first analyte and the second analyte; and wherein y is the first imaginary impedance, m is a slope, x is a target concentration, f is a frequency, and b is an intercept.

5. The method of claim 1, wherein said two or more different analyte-capturing molecules comprise an antibody.

6. The method of claim 5, wherein said antibody is against a lipoprotein.

7. The method of claim 6, wherein said lipoprotein is HDL or LDL.

8. The method of claim 1, wherein said electrode includes a self-assembled monolayer.

9. The method of claim 8, wherein said self-assembled monolayer comprises 16-mercaptohexadecanoic acid (MHDA).

10. A method comprising:

exciting an electrode with an electrical signal having multiple different frequencies, the electrode including a first analyte-capturing molecule and a second analyte-capturing molecule, the first analyte-capturing molecule binding to a first target analyte, the second analyte-capturing molecule binding to a second target analyte, the electrode having been contacted with one or more samples, the one or more samples including the first target analyte and the second target analyte;

receiving a first imaginary impedance response signal from the electrode that has been electrically excited;

decoupling the first imaginary impedance response signal to generate a second imaginary impedance response signal that includes a first peak representing a first target analyte and a second peak representing a second target analyte;

detecting the first target analyte in the sample from the first peak in the second imaginary impedance response signal; and detecting the second target analyte in the sample from the second peak in the second imaginary impedance response signal.

11. The method of claim 10, wherein the first target analyte is a first lipoprotein and the second target analyte is a second lipoprotein.

12. The method of claim 11, wherein the first target analyte is HDL and the second target analyte is LDL; and wherein the first analyte-capturing molecule is specific to HDL and the second analyte-capturing molecule is specific to LDL.

13. The method of claim 10, wherein the decoupling the first imaginary impedance response signal includes:

decoupling at a first predetermined optimal frequency of the first target analyte and at a second predetermined optimal frequency of the second target analyte.

14. The method of claim 13, wherein the first predetermined optimal frequency corresponds to a frequency of the first peak for the first target analyte; and wherein the second predetermined optimal frequency corresponds to a frequency of the second peak for the second target analyte.

15. The method of claim 13, wherein the detecting the presence of the first target analyte and the second target analyte in the one or more samples is devoid of using a real impedance from the electrode.

16. The method of claim 10, further comprising:

generating a first calibration curve using the first peak;

determining, using the first calibration curve, a first concentration of the first analyte in the one or more samples;

generating a second calibration curve using the second peak; and determining, using the second calibration curve, a second concentration of the second analyte in the one or more samples.

* * * * *